(12) United States Patent
Martens

(10) Patent No.: US 7,846,069 B2
(45) Date of Patent: Dec. 7, 2010

(54) EXERCISE SYSTEM WITH GRAPHICAL FEEDBACK AND METHOD OF GAUGING FITNESS PROGRESS

(75) Inventor: Mark H. Martens, Church, VA (US)

(73) Assignee: Pantometrics, Ltd., Falls Church, VA (US)

( * ) Notice: Subject to any disclaimer, the term of this patent is extended or adjusted under 35 U.S.C. 154(b) by 0 days.

(21) Appl. No.: 12/814,633

(22) Filed: Jun. 14, 2010

(65) Prior Publication Data

US 2010/0248901 A1    Sep. 30, 2010

Related U.S. Application Data

(63) Continuation of application No. 11/245,041, filed on Oct. 7, 2005, now Pat. No. 7,736,272, which is a continuation-in-part of application No. 11/000,920, filed on Dec. 2, 2004, now abandoned, which is a continuation-in-part of application No. 09/933,576, filed on Aug. 21, 2001, now abandoned.

(51) Int. Cl.
*A63B 71/00* (2006.01)
(52) U.S. Cl. .......... 482/8; 482/1; 482/9; 482/900
(58) Field of Classification Search .......... 482/1–9, 482/900–902; 434/247; 600/300, 324
See application file for complete search history.

(56) References Cited

U.S. PATENT DOCUMENTS

| | | | | |
|---|---|---|---|---|
| 5,207,621 | A * | 5/1993 | Koch et al. | 482/53 |
| 6,244,988 | B1 * | 6/2001 | Delman | 482/8 |
| 6,808,472 | B1 * | 10/2004 | Hickman | 482/8 |

* cited by examiner

*Primary Examiner*—Glenn Richman
(74) *Attorney, Agent, or Firm*—Miles & Stockbridge P.C.; Stephen W. Aycock, II

(57) ABSTRACT

A system and method for providing visual feedback to a user of an exercise machine for gauging fitness progress of the user. The system provides a user of an exercise machine with a virtual competition in which the user competes against virtual competitors based on his past performances or those of other users, either as an individual or as a member of a team. The team may also be part of a league. For an individual competing against his own past performance(s), the system may raise the level of performance required to win the virtual competition, and may also lower the level of performance required if the user is not performing well on a particular day. For an individual competing against others in either real-time or against designated results, either as part of a team or a league, the system may reduce the isolation, disconnection, and tedium often experienced by users of cardiovascular exercise equipment and provide a social outlet. The system attempts to keep the user engaged and motivated to achieve desired fitness goals by providing real-time performance data and historical performance data displayed in a graphical manner coupled with the entertainment and excitement of competition and social interaction.

11 Claims, 16 Drawing Sheets

EXERCISE SYSTEM WITH GRAPHICAL FEEDBACK AND METHOD OF GAUGING FITNESS PROGRESS

CROSS REFERENCE TO RELATED APPLICATIONS

This application is a continuation of application Ser. No. 11/245,041, filed Oct. 7, 2005 now U.S. Pat. No. 7,736,272, which is a continuation-in-part of application Ser. No. 11/000,920, filed on Dec. 2, 2004 (now abandoned), which is a continuation-in-part of application Ser. No. 09/933,576, filed on Aug. 21, 2001 (now abandoned), which are incorporated herein by reference in their entirety.

BACKGROUND OF THE INVENTION

This present invention relates generally to exercise equipment and more particularly to a cardiovascular exercise machine having a display system to provide a visual gauge of fitness progress and a method for gauging fitness progress.

Cardiovascular exercise machines, as used herein, include fitness bikes, treadmills, step machines, stair machines, rowing machines, cross country skiing machines and/or the like. These exercise machines have been equipped with a device comprising a combination of a visual display and a controller. For example, an exercise machine is known to have attached thereto a media system. The media system may provide capability to play compact discs and cassette tapes, as well as providing small television screens on which to view television programming, movies, and/or the like. In such machines, there is no electronic connection between the media system and the exercise machine. The media system merely provides the capability to watch TV and play music during workouts.

In another known exercise machine, monitors are attached in order to vary and monitor parameters of the workout such as resistance, target heart rate, time elapsed, distance covered, current pulse rate, caloric burn 'rate', and total calories consumed during the workout. The monitors may typically display numeric variables in pre-formatted areas, and grids of dots that are either lit, to produce bars of various heights. Once a user finishes the workout, summary information may be briefly displayed in numeric format, and then may disappear.

In yet another example of known exercise equipment, exercise machines are provided with Internet connectivity for use while exercising. This particular system may also provide for individual user identification, recording of total or cumulative miles of 'exercise' achieved for each identified user, and permit a user to view his or her own summary of historical totals while in the system. However, this display may be in the form of numerical data, possibly in a spreadsheet format.

There may have been products or services where a computer projects a paced competitor that proceeds at a specific pre-selected speed. In other systems a user may compete against other users. Although these systems may harness the competitive spirit, or alleviate exercise boredom for some, these systems suffer from several limitations.

For example, conventional exercise displays may not allow a user to determine whether the user is performing better, or worse, than in the past. For example, a user may want to determine if he or she can cycle (or run) faster, further, or easier today as compared with yesterday, or last week. Further, conventional exercise displays may not allow a user to determine how much energy was expended during their present workout as compared with a previous workout, except in total, and after they complete the workout.

A common concern of exercise machine users is whether they are improving their fitness. Conventional exercise machine displays may not allow a user to determine if the user is improving his/her fitness, and, if so, by how much, and in what way.

Another common concern of exercise equipment users is whether they are more fit currently than they were in the past. Conventional exercise displays may not allow a user to determine, for example, whether the user is more fit today than the user was yesterday, last week, or last month, and, if so, by how much and in what way.

Yet another concern of users of exercise machines may be about what needs to be done immediately in order to reach a desired performance level. Conventional exercise machine displays may not allow a user to determine how much harder the user has to exercise in order to reach a desired performance goal. Further, conventional exercise machine displays may not allow a user to determine how much harder the user should exercise immediately in order to improve performance.

A still further concern of exercise machine users may be determining average performance during exercise sessions and what the trend of the average is.

Conventional exercise displays may not allow a user to determine how tired the user was at a similar point in a previous workout. Further, conventional exercise machine displays may not allow a user to determine if a user is capable of beating the user's fastest, or best, time because conventional exercise displays may not allow a user to determine the user's best performance achievement to date for specific distances, or durations.

A major concern of exercise machine users is determining whether there has been any measurable progress made toward the user's goal of improving their fitness.

A difficulty in exercise programs may be that regular rigorous exercise is hard to maintain. For example, many people may start exercise programs with great enthusiasm, but may quickly lose motivation after a few weeks. According to research, approximately 60% of new members joining gyms to start an exercise program may give up after 3 months. At the beginning of a new year, consumers may spend thousands of dollars on exercise machines, and, within a few months, the exercise machines may be gathering dust in a basement. For many people, it may be difficult enough to get motivated to start exercising in the first place, and may be even more difficult to maintain high exercise intensity for a full 20-30 minute workout. Although many people may be highly motivated to exercise for self-improvement, for most, aerobic activities, particularly using exercise machines, may be hard work, tedious, repetitive, uncomfortable, and/or boring.

Conventional visual systems on or around exercise equipment attempt to address these concerns. While some visual display systems may alleviate the tedium felt during repetitive motion exercise, they may also be distracting to the workout itself.

Although conventional systems may make the user less bored during exercise, they may not make the user less bored by exercise. For example, watching a great basketball game on a television display system while exercising may be entertaining, but it may not help a user get a better workout. In fact, quite the opposite may result. Such systems may entertain the user, but at the cost of further disconnecting the user from the exercise activity. They may also impair a connection to the exercise activity and an ability to engage in intense workouts.

Activities like television or surfing the net, available on exercise equipment, may make one more likely to come to the gym, but because they may distract the user from the workout, they may reduce the intensity of the exercise program. Yet for fitness improvement, it may be critical for a user to push beyond his limitations, and for this reason, an increase in workout intensity may be necessary. In other words, it may not be enough to be 'less bored' during exercise activity for fitness improvement. Rather, a user may need to feel more invested in the activity itself.

Exercise frequency is important, but without workout intensity improvements may be very limited. For intense workouts, motivation and concentration may be critical. Because conventional systems may actually make it more difficult to concentrate and work out hard, users may experience limited fitness improvements even after using such exercise machines for long periods of time. As a result, they may get both bored and disappointed, leading to a possible discontinuation of the exercise activity.

Conventional exercise machine display systems may periodically display limited variables such as the user's current heart rate in numerical format. In contrast, the present invention allows the user to view graphs and charts showing continuously changing variables (such as pulse rate) in real-time from the initiation of the workout. This real-time graphical representation allows a user to continuously monitor and adjust relative effort, intensity, and duration, as well as progress and self-improvement.

A further deficiency in conventional exercise equipment is, that they isolate users from each other. Conventional exercise machine display systems do not provide for communication, competition, or interaction among users because, at best, said conventional systems are only connected to the same brand and/or 'types' of exercise equipment. In contrast, the current invention allows users of different models or even different types of equipment, from different vendors, in different places, and at different times, to mutually identify workout partners, to permit others to use their stored workouts as pacers, or even to compete against others in real-time. The Fitclub system can allow users to use different types of machines from different vendors by maintaining the relevant distance calibration for each model in the database as shown in the machine model distance table (718) in the drawing in FIG. 7. The present invention also allows a user to send and receive messages to and from other users while working out, and to make those messages accessible to other users both in real-time, or later during the receiver's workout. The current invention also allows individual users to cooperate with others in their workouts as members of teams or leagues, in real-time or with previously saved workouts. The current invention provides these capabilities for users exercising on equipment directly next to each other, in the same exercise facility, or in exercise facilities or homes across the world.

With some known exercise machines, users are able to choose a variety of pre-programmed workout environments, in which the user's virtual figure "exercises." These various environments are generic and often involve a "country" landscape or a "mountain" landscape. The present invention, by contrast, allows users to choose from a variety of true-to-life routes on which to exercise by cycling, running, or other cardio activity, and to do so in real-time with others in the same 'virtual place'. These real-time, real-life landscapes include Washington, D.C., New York City, and the Tour de France, as well as many other virtual location scenes, either actual or fictional.

SUMMARY OF THE INVENTION

An exemplary embodiment of the present invention provides a solution to the problem and limitations of conventional display system discussed above by creating a real-time visual feedback environment in which the user may exercise in a virtual competition. In the virtual competition, a user exercises against his/her own previous workouts as "shadow competitors", while continuously receiving updated graphical presentations of relevant performance and physiological parameters, based on the current workout and in relation to those of previous workouts. An exemplary embodiment of the present invention comprises a local computer, or processor attached to an exercise machine, a visual display device, processes, software, drivers, graphical animation methods, and a remote server(s) and database. This embodiment uses a separate local computer for each client, but the system may work in an equivalent fashion with a single local server providing the processing. This embodiment of the present invention provides a method and system for measuring, recording, and providing graphical and/or visual feedback to users of the relevant parameters of their current workouts, juxtaposed with those of their own previous workouts, or with those of other user(s), who have permitted them to do so, on exercise machines. The system may work in an equivalent fashion, in real-time competitions, and with minor adjustments, for many different cardiovascular exercise machines.

In an exemplary embodiment of the present invention, the display system of the invention may be attached to an exercise bicycle. In this embodiment, the local system visual display mechanism (for example, a monitor attached to an exercise bike) presents a small cyclist figure representing the current workout of the user. The figure may move along a "virtual track" on the display screen, varying in relation to the rate at which the user is pedaling. The invention may also produce several other "shadow competitor" cyclist figures. The other shadow competitors may represent actual and/or theoretical workouts previously recorded, which may be averages, or the user's best performance results or may be other users who have given permission for their results to be used in a competition, either as an individual, or a member of a team or a league. Each of the shadow competitors may move along the virtual track at a rate in accordance with the speed at which the user pedaled during an actual workout. In addition to reproducing into the current virtual environment actual workouts previously recorded, the invention also generates mathematical or even theoretical shadow competitors to represent, for example, a weekly, monthly, team, or any other average, or for such things as the personal best time.

In addition to creating the 'virtual competition', an exemplary embodiment of the present invention may provide a continuous record of all workout variables from the beginning of the workout to the present time in graphical format. For example, the user may see not only what his current pulse rate is, but the user may see a line graph of exactly what it is at each point in the workout and how the user's pulse rate has been changing throughout the workout. To allow for comparisons with previous workouts, an exemplary embodiment may also provide the user with an input device, such as, for example, a touch screen, to bring up the same graphical representations for each and any of the "shadow competitors." These graphs may be juxtaposed, or overlaid, with the current graph for that variable to provide the user with immediate up to date visual comparisons. This allows the user to readily see, for example, how his current pulse rate has changed compared to his/her pulse rate on a previous workout, up to this same point in the workout.

The visual juxtaposition, or overlay, of workout shadows allows the user to easily and immediately see whether the user is ahead or behind a particular shadow(s), and by how much. The graphical juxtaposition, or overlay, of workout variables such as pulse rate also allows the user to readily ascertain the relative intensity and relative fitness compared to specific previous workouts, at each point throughout the workout. This feedback may keep a user involved in a workout and provide an incentive to work harder.

The invention, in an exemplary embodiment, thus provides visual representations in real-time, of 'up-to-date' workout intensity and progress or change over time, as the user is achieving it. The present invention may be designed to make the workout more personal, more interesting, more compelling, and/or provide the greater motivation. Visually, the system may mimic watching oneself compete on television in a representation of an actual place, without ever actually being there. Although previously exercise may have been a solitary and boring activity, the visual feedback system of the present invention on relative workout performance, in real time, may provide for an interesting competition, and also provide immediate visual feedback on many aspects of the workout as well as improvement over time. The present invention may overcome the limitations of conventional systems by combining physical and/or physiological feedback relative to previous workouts, which may provide psychological reinforcement for increasing intensity and self-improvement.

In an exemplary embodiment of the present invention, each user may choose to compete against himself. This may be important for psychological reasons. Unlike competing against others, this is a competition that all users can win most of the time, providing more encouragement and therefore incentive to try harder. In fact, on any given day, each user may have a chance to win their race. However, each time they do, it raises the performance bar for next time. The more often one beats a shadow competitor, the better performance it takes to beat the shadow competitor the next time, but also the more the user pushes his/her body to improve it's capabilities. Conversely, after a few slower weeks, a user may be temporarily discouraged, but the performance bar is being lowered, which gives the user a better chance of doing well the next time period. It is this finely tuned 'automatic adjusting of the performance bar' that an exemplary embodiment of the present invention provides, which constructs an appropriate schedule of positive psychological reinforcement and therefore encouragement. To maximize motivation, an exemplary embodiment of the present invention may make each workout challenging, but not discouragingly so, for each user based on their abilities and past performance.

Another exemplary embodiment of the present invention shows measurable progress towards a fitness goal in a way that may also provide an incentive and reward for effort. By providing feedback in a current workout, the system may encourage a user in real-time, when the user's motivation is most vulnerable.

In other words, the system and method of the present invention may make a computer game out of workouts. Millions of people play computer games long and often, and, perhaps, even obsessively. Although this may sound like unproductive or frivolous behavior on a computer game, it is exactly the behavior to encourage for exercise activities. Therefore, the system and method of the present invention may be designed to take advantage of the same psychological forces by creating the same environment. Only in this game the "joystick" is an exercise machine, the "skill" is workout effort, and the only way to win the game is to workout harder. Normally obsessive gaming leads to "sore thumbs", but by attaching a different game console and joystick, this invention actually harnesses obsessive behavior to get "sore muscles", and fitness improvements.

Further, in this exemplary embodiment, a user may, with the permission of other users, choose to exercise or race against their workout partner's already completed and stored workouts as a 'shadow competitor'. In the exemplary embodiment, the user will be permitted to add or remove the userIDs of their designated partners on a form on the website at any time. The user's choice of designated workout partners will be kept on the remote database in a table like 902 in FIG. 9 of the drawings. In the exemplary embodiment, when the user logs on, they will then be allowed to choose from a list of their own saved workouts and those of users who have designated them as workout partners.

In the exemplary embodiment, a user may also choose to communicate with other users while working out in real-time. Each time a user logs on to the system, a flag is entered into the database in table 708, identifying their presence in the system and the ID of the individual machine they are on in table 706. In the exemplary embodiment, users will be prompted to communicate with their workout partners if any of them they are simultaneously logged on to the system, in accordance with the flow shown in FIG. 11. Or they may send messages for workout partners or any other users, in accordance with the flow shown in FIG. 10 by using their e-mail address as shown in table 708.

Another exemplary embodiment of the present invention provides for communications, and interactions among users and health clubs. In the conventional exercise environment, even in those scenarios where perhaps hundreds of other users are physically present, a user is isolated from his fellow exercisers as he operates a piece of exercise equipment. This disconnected and isolating experience, which occurs in the midst of so many other people, often leads users to discontinue their exercise pursuits. In contrast, an exemplary embodiment of the present invention provides for users to mutually identify work-out partners in the system (stored in table 902), to permit those partners to mutually retrieve and compete against each others saved workouts, and to allow users to communicate with other users in real time, or leave messages for them to retrieve during their next workout on the GWFS.

In the exemplary embodiment, the graphical workout feedback system (GWFS) provides via the website, the capability for users to define and administer leagues and teams within the system, and to establish durations, criteria, and reward systems for those leagues. This data will be administered as shown in FIG. 12 of the drawings. In this embodiment the GWFS will allow users to make the leagues as narrow or as broad as they wish for example: 'over 40, female members of Golds Gym'. In the exemplary embodiment, eligibility for those leagues will be assessed automatically by the system based on the information retained on member users. In the exemplary embodiment, each individual workout may be attributed to one, two, or as many leagues or teams as they want simultaneously.

In yet another exemplary embodiment, f the present invention comprises a remote data system, a website, a local system, and a method of connecting the remote and local systems.

The remote system comprises a remotely located web and database server(s) which may or may not be co-located, with installed operating system(s), accessible by a large number of local systems, a database, and transmission and communication protocols, and operating system, software technologies, and application programming interfaces (APIs).

The local system comprises a computer and monitor connected to an exercise machine, a set of sensors and drivers for measuring user workout activities/motions on the machine and transmitting them to the system in electronic form, transmission and communication protocols, routers, interface/query programs for sending and retrieving workout data to and from remote database, as well as the software implementing the user interfaces, the graphics, the 3D animation functionality. The animation functionality comprises 3-dimensional visual representations of current and previous actual or mathematically constructed workouts in the same time/space reference (e.g. figures representing the current exercise activity 'competing against ones own previous workout/time'), 3-dimensional terrains and models of actual places, and objects, as well as graphical presentations of different parameters of current and previous workouts, such as distance covered, resistance, and pulse rate, up to date, in real time, and throughout the duration of the workout.

The connectivity between local and remote systems may be a wired or wireless network, such as, for example, the Internet.

BRIEF DESCRIPTION OF THE DRAWINGS

The present invention will be described with reference to the accompanying drawings, wherein.

DETAILED DESCRIPTION

Figure 1:
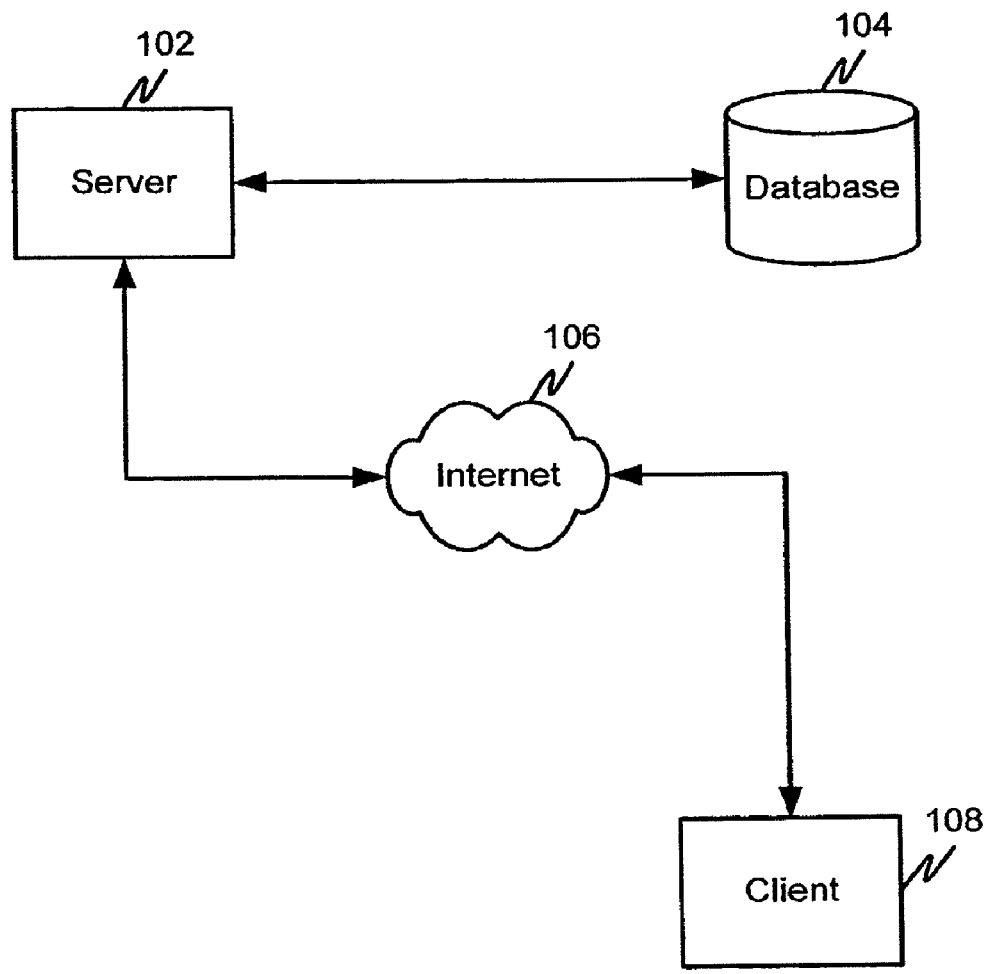
FIG. 1 is a block diagram of a conventional client server database architecture with internet connection.

Referring to FIG. 1, there is illustrated a block diagram of a conventional client server database system with Internet connection. In particular, client server system 10 comprises a server 102, a database 104, an Internet network 106, and a client 108.

Figure 2:
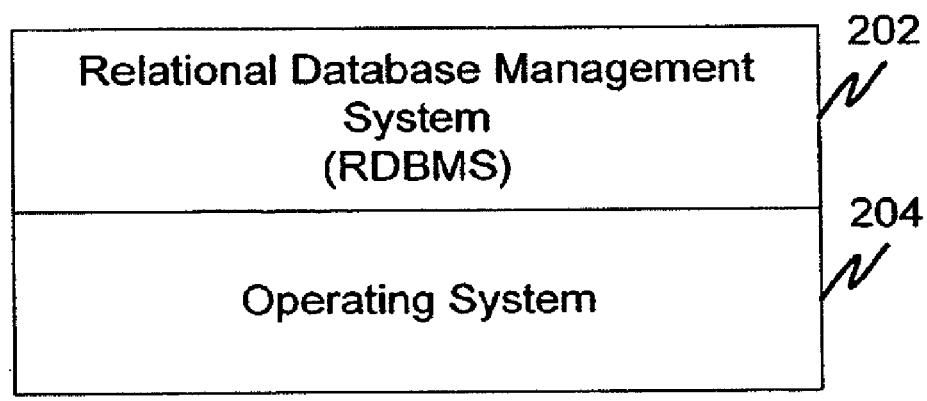
FIG. 2 is a block diagram of a server side software architecture showing a relational database management system in relation to an operating system.

FIG. 2 is a block diagram of a relational database management system in relation to an operating system. In particular, a relational database management system 202 is coupled to an operating system 204.

Figure 3:
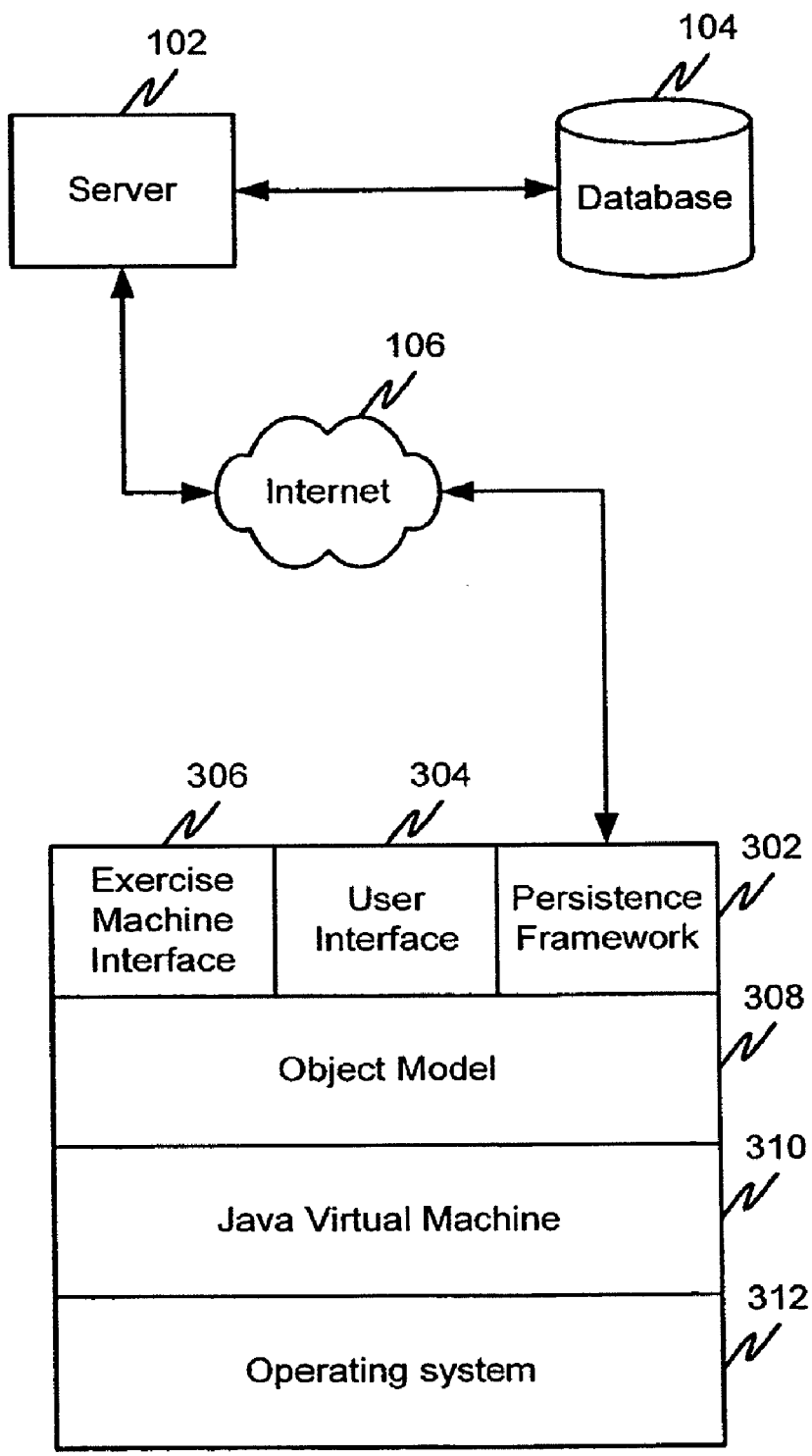
FIG. 3 is a block diagram of an exemplary client software architecture in relation to a network architecture for the present invention.

FIG. 3 is a block diagram of an exemplary client architecture in accordance with the present invention. In particular, a client architecture comprises a persistence framework (e.g. Hibernate) 302, a user interface (e.g. SWING) 304, an exercise machine interface 306, a relational database design (e.g. MYSQL) 308, a java virtual machine 310, and an operating system (e.g. Linux) 312.

In operation, the persistence framework 302 provides a mechanism for the GWFS application data to be permanently saved. The user interface 304 provides the graphical user interface functionality. The exercise machine interface 306 provides an interface to the sensor coupled to the exercise machine and/or the user. The object model 308, java virtual machine 310, and the operating system 312 provide various software support services that enable the GWFS application to operate.

Figure 4:
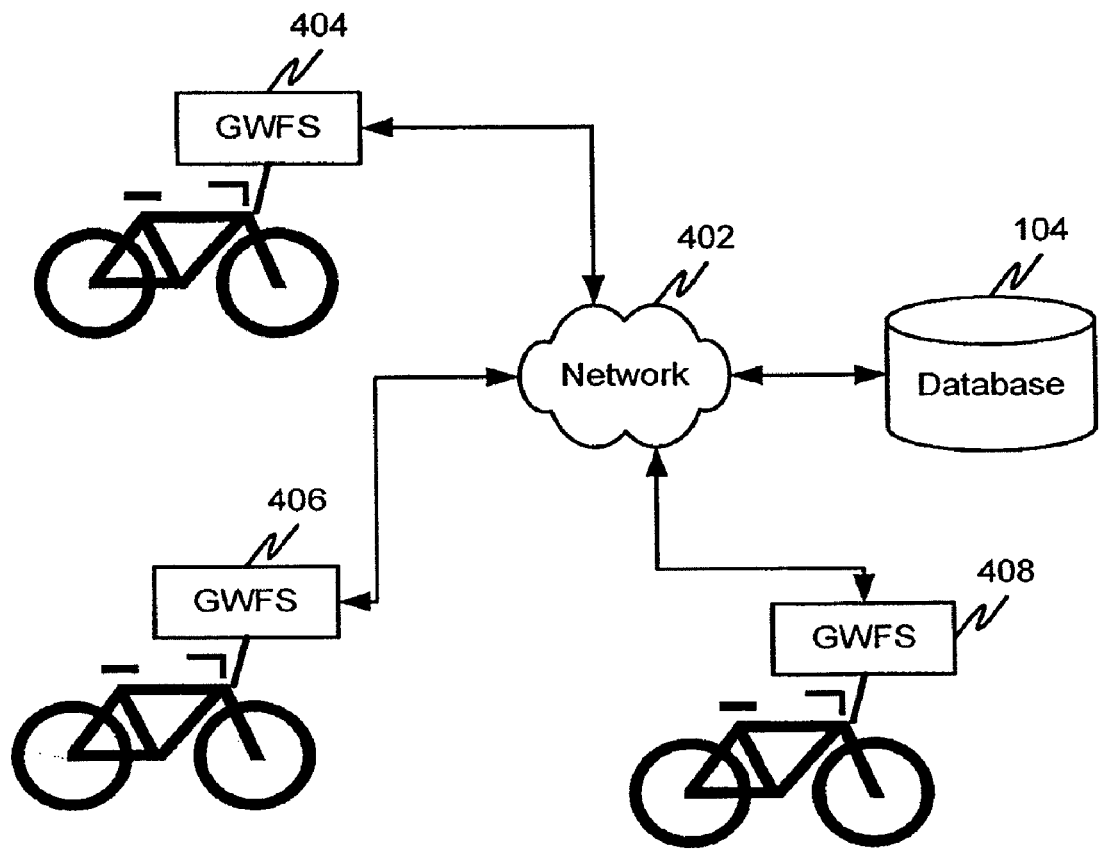
FIG. 4 is a block diagram of an exemplary exercise machine network in accordance with the present invention.

FIG. 4 is a block diagram of an exemplary exercise machine network in accordance with the present invention. In particular, a database 104 is linked to a network 402. Exercise machines equipped with the GWFS (404, 406, and 408) are linked to the network 402.

In operation, the exercise machines equipped with the GWFS (404, 406, and 408) store and retrieve data in the database 104 via communication across network 402. The network 402 may be a wired or wireless network.

Further, the system provides for individual user identification and confirmation. User input is accomplished by the local part of the system, the GWFS units (404, 406, and 408), which are attached to the exercise machines. The GWFS units (404, 406, and 408) prompt the user to enter information identifying the user and intended workout parameters. The visual display of the GWFS units (404, 406, and 408) provides this functionality through a touch-sensitive monitor screen keyboard that is displayed in response to the user initiating the system. The touch-sensitive screen keyboard is a preferred, but not the only, method for the local system interface, and is desirable primarily for eliminating the need for a physical keyboard. The system is initiated when a user touches the application icon, or when a user commences to use the equipment in the normal manner. If the user requests GWFS functionality the local system sends a query to the remote database 104, via the network 402 using identification information input by the user. As soon as the local part of the system authenticates the user from the remote database, it returns their previous workouts, allows the user to select form those workouts, and then it creates a 'virtual competition' environment on a selected area of the visual display (monitor). The system generates different virtual competition environments depending on the particular exercise machine it is attached to. For illustrative purposes the current description assumes it is attached to an exercise bike. In this case, the virtual competition environment consists of a road, or track (circular, linear, or other shaped course) in which cycling figures can be depicted. The GWFS units (404, 406, and 408) depict the current workout as a figure on a bike moving along the track at a speed commensurate with the rate at which the user pedals on the exercise machine. The system moves the 'cyclist' around/along the virtual track much in the same way a video game does. But the GWFS in this configuration responds to pedal motion not to input from a joystick or game console. This functionality is accomplished using various graphical animation methods.

When the remote server (not shown) receives the identification request from the local GWFS units (404, 406, and 408), it verifies the user identification and returns a package of data to the local site, i.e. the GWFS units (404, 406, and 408). This package of data is typically a standardized profile of the user's previous workouts.

The initial standard data package depends on the recency and availability of previous workout data. The GWFS units (404, 406, and 408) temporarily store this data on the local hard drive, and then use this data to generate a variety of 'shadow competitors' and add them to the visual presentation of the virtual competition. One shadow competitor is generated for each previous workout retrieved. For example, if the individual has already been working out for a minute by the time the local system receives the data package, then the GWFS presents each shadow competitor at the logical location on the virtual track that was reached, one minute after the start of each respective workout. Each shadow competitor is color coded for easy visual identification and with a color intensity in reverse proportion to the recency of that workout. For example, if a shadow represents a workout from a month ago, the shadow would have a very low color intensity. The local system also generates shadow competitors for theoretical workouts such as 'the previous weeks average', the 'previous months average', 'weekly average to-date', 'personal best', and others. A preferred number of shadow competitors, depending on several conditions, is 5-10. The standard competition includes the previous five workouts, plus a shadow for the average (of those five), plus a shadow for the user's personal best time for that workout distance. In any case, it is likely that the virtual competition will function best based on a total of less than 10 total shadow competitors. However, the GWFS units (404, 406, and 408) also generate more shadow competitors in response to subsequent user requests.

The GWFS units (404, 406, and 408) recreate the exact movement over time of those previous workouts, but depict them as shadow competitors moving along the same virtual track as the current workout. Each shadow is depicted either behind or ahead of the current workout figure, and each other, at all times in exact proportion to their relative performance from the initiation of the workout. In other words, the GWFS units (404, 406, and 408) take all these workouts that occurred in reality at different times, and recreates them, in the same track, as if they were happening simultaneously. It should be appreciated that the graphical presentation may be in two-dimensional graphics, or in three-dimensional graphic representations. With a result that the GWFS creates a visual effect similar to a real-time computer game using a virtual competition with oneself.

Figure 5:
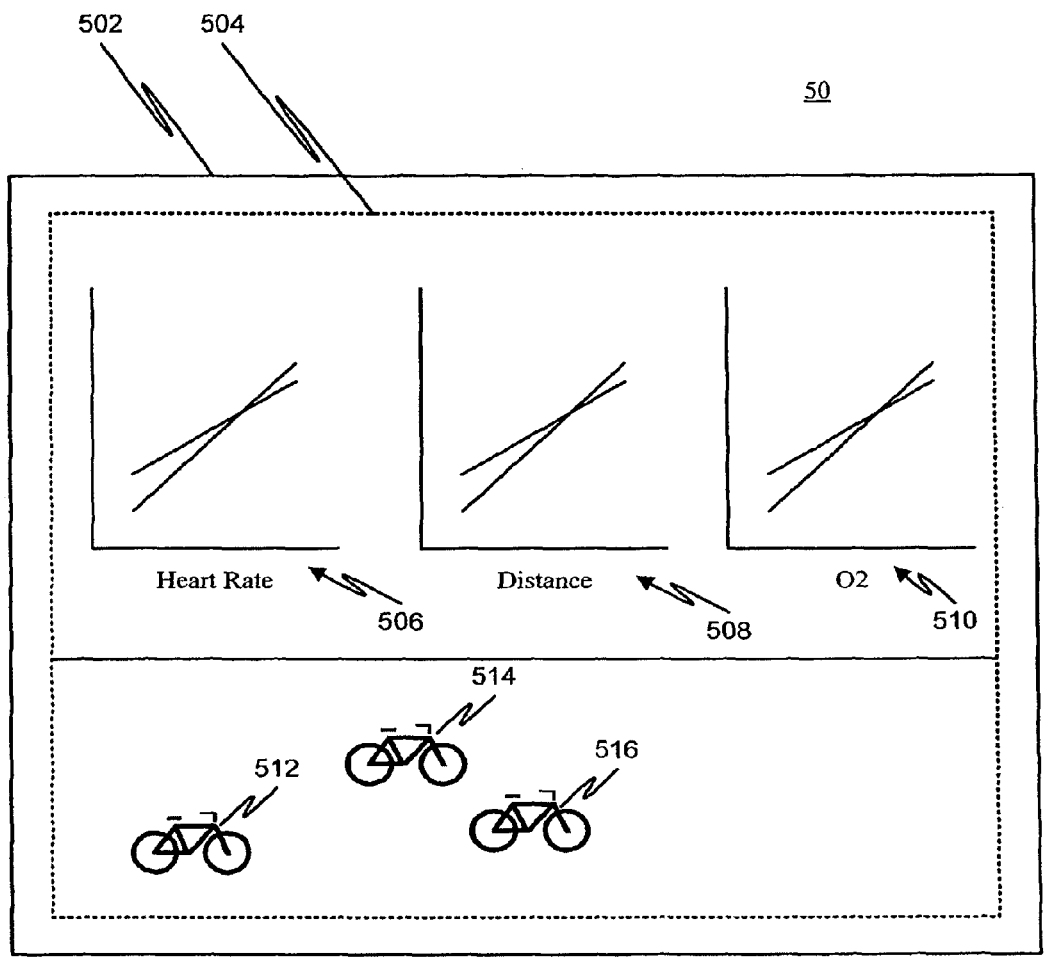
FIG. 5 is a diagram of an exemplary graphical user interface display in accordance with the present invention.

FIG. 5 is a diagram of an exemplary user interface in accordance with the present invention. In particular, a display system 50 comprises a visible screen portion 502, a touch screen portion 504, a heart rate graph 506, a distance graph 508, a blood oxygen level graph 510, a first virtual competitor 512, a second virtual competitor 514, and a graphical symbol of a current workout 516.

In operation, the heart rate graph 506, distance graph 508, and blood oxygen level graph 510 are responsive to data received from sensors attached to the user or to the exercise machine. The first virtual competitor 512 and second virtual competitor 514 are responsive to historical data retrieved from a database. The graphical symbol of a current workout 516 is responsive to current workout sensed data. The touch screen portion 504 is responsive to user input.

Further, the graphics necessary for the basic visual presentation and functionality of the graphical user interface are retained on, and generated by, the local GWFS. Because the required graphics images are known prior to run time, this is not a problem. It should be appreciated that many different competition environments, or 'tracks' could be easily provided as options to the user. The GWFS is configured so that communications between remote and local systems are in the form of conventional protocols, but may be implemented in later developed protocols. By transmitting only data, bandwidth requirements can be kept to a minimum for this functionality.

Conventional systems may provide methods for measuring, recording, and presenting summary information on exercise machine workouts. Known exercise bikes, for example, display (for a few seconds at the finish of the workout); the total number of miles cycled, total number of calories, burned, and total time duration. However, even if systems retained summary information such as that the current user covered 4.86 miles in the previous 15-minute workout, this would provide sub-optimal estimates for creating a virtual competition, and inadequate records for graphical presentations and real time feedback. To remedy this problem the local system of the current invention measures and records several aspects of each workout, in small increments, throughout the duration of the exercise activity.

For some workout variables, such as the pedaling rate and resistance, the GWFS measures and records one or more times per second, others such as pulse rate are recorded at larger intervals, such as once per minute. The GWFS uses straight-line extrapolation to smoothly bridge from one measurement point to the other for those workout variables that are recorded at larger time intervals. Tradeoffs and compromises may have to be made between the number of variables measured, the measurement interval, the number and size of shadow figures, number of dimensions, graphical views and other variables depending on system processing or memory resources. There are many permutations that work perfectly well, and the specific combination is not critical to the functioning of the invention, although at extremes it may affect the degree of realism perceived by users.

On some conventional equipment the variable known as 'level' is actually a parameter that varies resistance to the pedaling activity. In the real world this is equivalent to a gear on a bike. A higher gear is a higher resistance level, but covers more distance, per revolution. However, in the current art no accommodation is made of how the resistance variable impacts distance covered. In fact, on some known exercise bikes, pedaling for half an hour causes the display to read the same 10.8 miles covered each time, regardless of the resistance level or even revolutions per minute (RPM) of pedaling. Although varying the level and RPM parameters causes these machines to report different results for 'calories burned', it is quite clear that measures generated by some conventional systems are gross, unrealistic, and unreliable. To more realistically reflect distance covered in a manner similar to an actual bike ride in the real world, the GWFS calculates the distance covered using the RPM directly and by multiplying this by an increasingly large factor as the level is increased. Thus the distance covered after ten seconds of pedaling at 100 RPM at resistance level six will be 1.x times as much as the same time and RPM at resistance level five. Calculation of the correct relative distance ratios for each resistance level is obviously an iterative process requiring a different calibration that varies by specific type of exercise equipment, and even by model or version. One of ordinary skill in the current art understands that the specific multiplier for each resistance level is subject to some tweaking, and may even have to vary (ultimately) according to the specific machine brand and model. Nevertheless, the GWFS is designed to consistently and credibly maximize the accuracy of such variables to minimize user disconnectedness from the workout activity, in sharp contrast to methods used in the current art. In practical terms, all the system needs to do to provide a substantial improvement is to have the distance increase with increasing revolutions per minute, not to measure it precisely. The formula for calculating distance will inevitably be approximate initially and improve over time.

Although the conventional systems may provide sensory devices on handles attached to the equipment for measuring pulse rates, these methods are not considered sufficiently accurate or reliable. In a preferred embodiment, the GWFS utilizes a different device that receives sensory information from a source closer to the heart. The device is a sensory device worn like a strap over the shoulder, resting directly over the chest and receiving sensory input through the chest rather than the hands. Such devices are currently available commercially as stand-alone pulse rate measurement devices. This GWFS invention will utilize such devices but will integrate them into the system by directly wiring the sensory device to the GWFS. Those of ordinary skill in the art will recognize that, wireless technology will perform this function equally as well as a physical wiring. The methods to integrate data from this device are also relatively straightforward and well known in the current art. In this configuration the GWFS records the pulse rate continuously using the sensory device, but then instead of replacing previous measurements with new ones as in the current art, the GWFS retains and stores the recorded pulse rate every 60-120 seconds on the local system. As with new data on all parameters, the GWFS then immediately updates graphical presentations. Those of ordinary skill in the art will recognize that it may be desirable to also measure such variables as blood oxygen level, oxygen intake, respirations, and/or the like. These variables vary significantly during intense aerobic activity, and the means to measure, record, and display them are known to the current art, although they are typically utilized in sports medicine or hospital situations. The system and method of the present invention may enable the same level of sophistication to be achieved on exercise machines in a gym.

Figure 6:
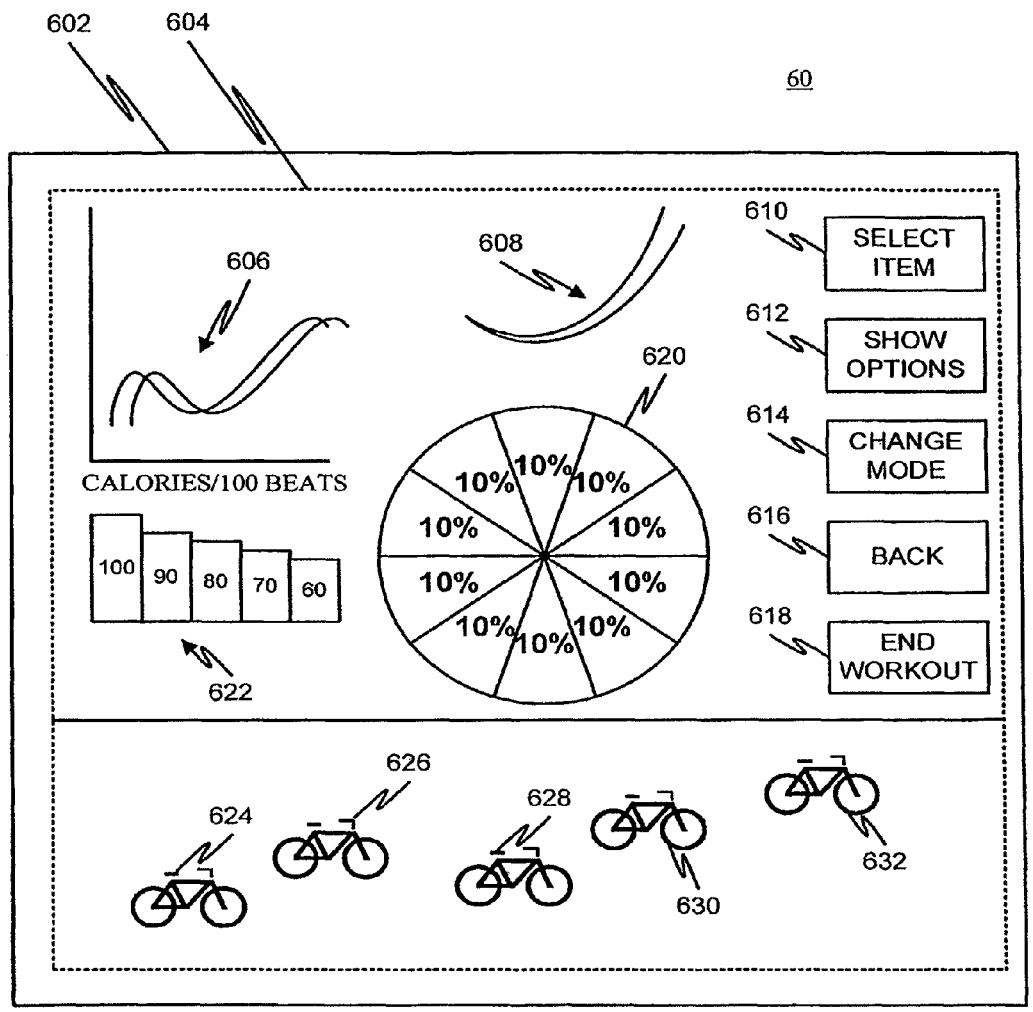
FIG. 6 is a diagram of an another form of a graphical user interface display in accordance with the present invention.

FIG. 6 is a diagram of an exemplary user interface in accordance with the present invention. In particular, a display system 60 comprises a visible screen portion 602, a touch screen portion 604, a calorie chart 606, a performance graph 608, a select item button 610, a show options button 612, a change mode button 614, a back button 616, an end workout button 618, an annual pie chart 620, a weekly improvement bar chart 622, a first virtual competitor 624, a second virtual competitor 626, a third virtual competitor 628, a fourth virtual competitor 630, and a fifth virtual competitor 632.

In operation, the select item button 610, show options button 612, change mode button 614, back button 616, and end workout button 618 are provided for receiving control input from a user. The calorie chart 606, performance graph 608, annual pie chart 620, and weekly improvement bar chart 622 are responsive to current and/or historical workout data. The first virtual competitor 624 represents a workout from ten days ago. The second virtual competitor 626 represents last week's average performance. The third virtual competitor 628 represents yesterday's workout. The fourth virtual competitor 630 represents today's workout. The fifth virtual competitor 632 represents the best performance of the user. The virtual competitors are responsive to historical and/or current data.

The buttons (610-618) are graphical symbols on a touch screen interface and respond to touch pressure from the user applied to the screen. While specific user interface elements are shown in FIG. 6, it should be appreciated that the user interface elements may be implemented in a variety of forms.

Figure 7:
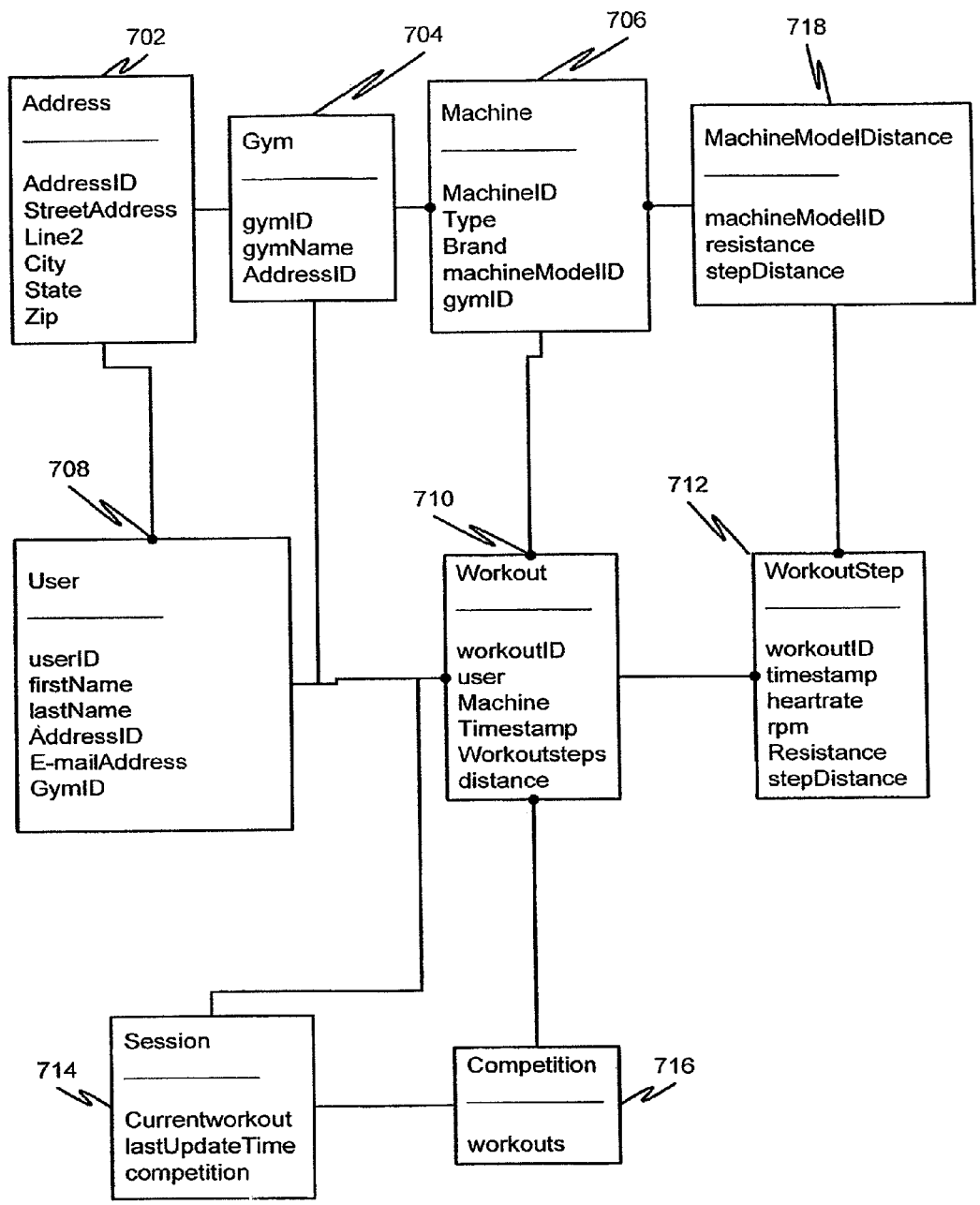
FIG. 7 is a block diagram of an exemplary relational database design in accordance with the present invention.

FIG. 7 is a block diagram of an exemplary software relational database design in accordance with the present invention. In particular, an address table 702 has a one-to-one relationship with a Gym table 704, a one-to-many relationship with a user table 708, and comprises six elements: 1) UserID, 2) Address1, 3) Address2, 4) City, 5) State, and 6) Zip. The Gym table 704 has a one-to-many relationship with a Machine table 706, the user table 708, and a workout table 710, and a one-to-one relationship with the address table 702, and comprises three elements: 1) GymID, 2) Name, and 3) Address. The Machine table 706 has a many-to-one relationship with the Gym table 704, a one-to-many relationship with the workout table 710, and comprises five elements: 1) MachineID, 2) Type, 3) Brand, 4) Model, and 5) GymID. The User table 708 has a many-to-one relationship with the Gym table 704, and the Address table 702, and a one-to-many relationship with the workout table 710, and comprises five elements: 1) UserID, 2) firstName, 3) lastName, 4) Address, and 5) GymID. The Workout 710 table has a many-to-one relationship with the Gym table 704, the User table 708, and the Machine table 706, and a one-to-many relationship with a WorkoutStep table 712, and comprises six elements: 1) workoutID, 2) userID, 3) machineID, 4) timeStamp, 5) WorkoutSteps, and 6) distance. The WorkoutStep table 712 has a many-to-one relationship with the Workout table, and comprises five elements: 1) workoutID, 2) timeStamp, 3) heartrate, 4) rpm, and 6) resistance.

Figure 8:
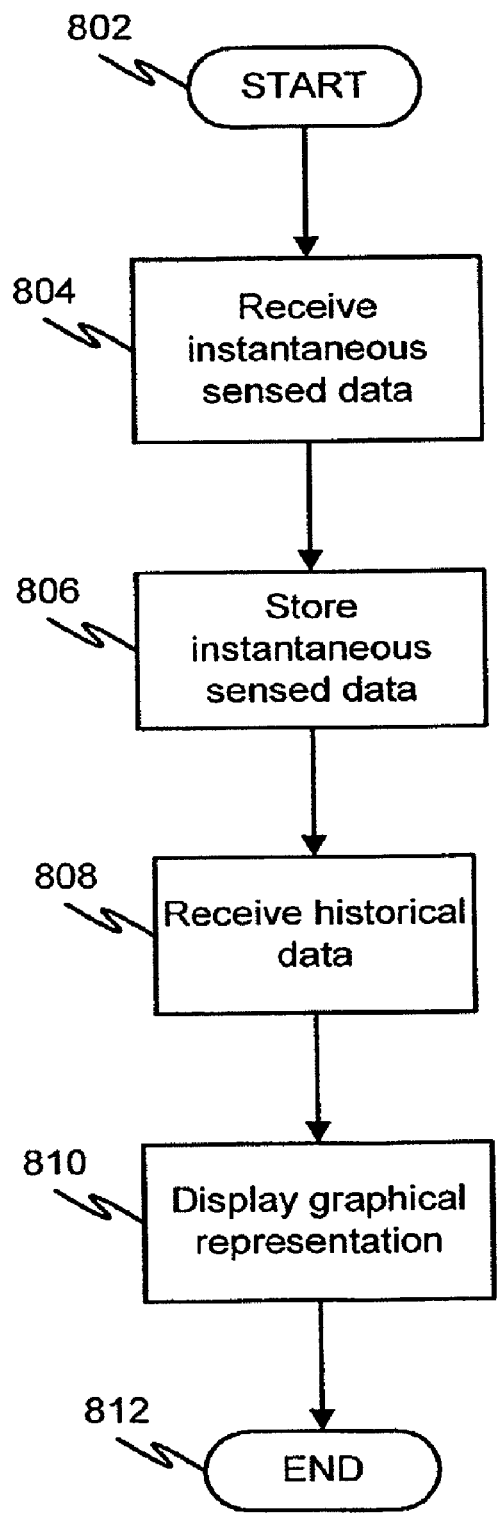
FIG. 8 is a flowchart of an exemplary method for providing graphical workout feedback in accordance with the present invention.

FIG. 8 is a flowchart of an exemplary method for providing graphical workout feedback in accordance with the present invention. In particular, the control sequence begins at step 802 and continues to step 804. In step 804, instantaneous sensor data is received by the graphical workout feedback system. Control then continues to step 806.

In step 806, the instantaneous data is stored. Control then continues to step 808. In step 808, historical data is retrieved. Control continues to step 810.

In step 810, the GWFS renders a graphical representation of the current workout instantaneous sensed data and the historical data. Control then continues to step 812 when the control sequence ends. However, the nature of the GWFS may require that control remain in a loop. In such an embodiment, control would continue from step 812 back to step 802 and the control sequence would begin again. Such a control loop may operate until terminated by a user, by power off, or by other source.

During the workout activities, all information relating to the workout is recorded and stored on the local system hard drive. As the workout proceeds, and as designated memory is allocated, the local system can periodically copy 'a partial chunk' of the current workout data and attempt to transmit it to the remote system to be stored in the database. This allows that storage to be freed up, if the local system threatens to run out. The optimal size or periodicity of these transmissions is between 1-5 minutes of (completed) workout data, depending on the connectivity, usage, and other factors. At the conclusion of the workout, during periods of 'down time', and based on availability of connectivity, the local system communicates with the remote system to insure that all data related to complete workouts have been received by the remote system and stored on the remote database. After confirmation of receipt from the remote location, the local system deletes the local copies of workout data on the hard drive, and releases the storage, whether it is needed or not.

In a preferred embodiment, the GWFS segments the visual display into three parts. It allocates the ongoing virtual competition to one area of the visual display, graphs of workout data to a second area, and user input icons to a third area. Optimally, the far right part of the visual display screen (a column approximately 20-25% of screen width) be allocated to user input icons, and the remaining portion of the visual display is segmented by a horizontal line approximately ⅓ of the way down from the top. In the optimal configuration the virtual competition is presented in the larger ⅔ portion at the bottom of the screen.

Figure 9:
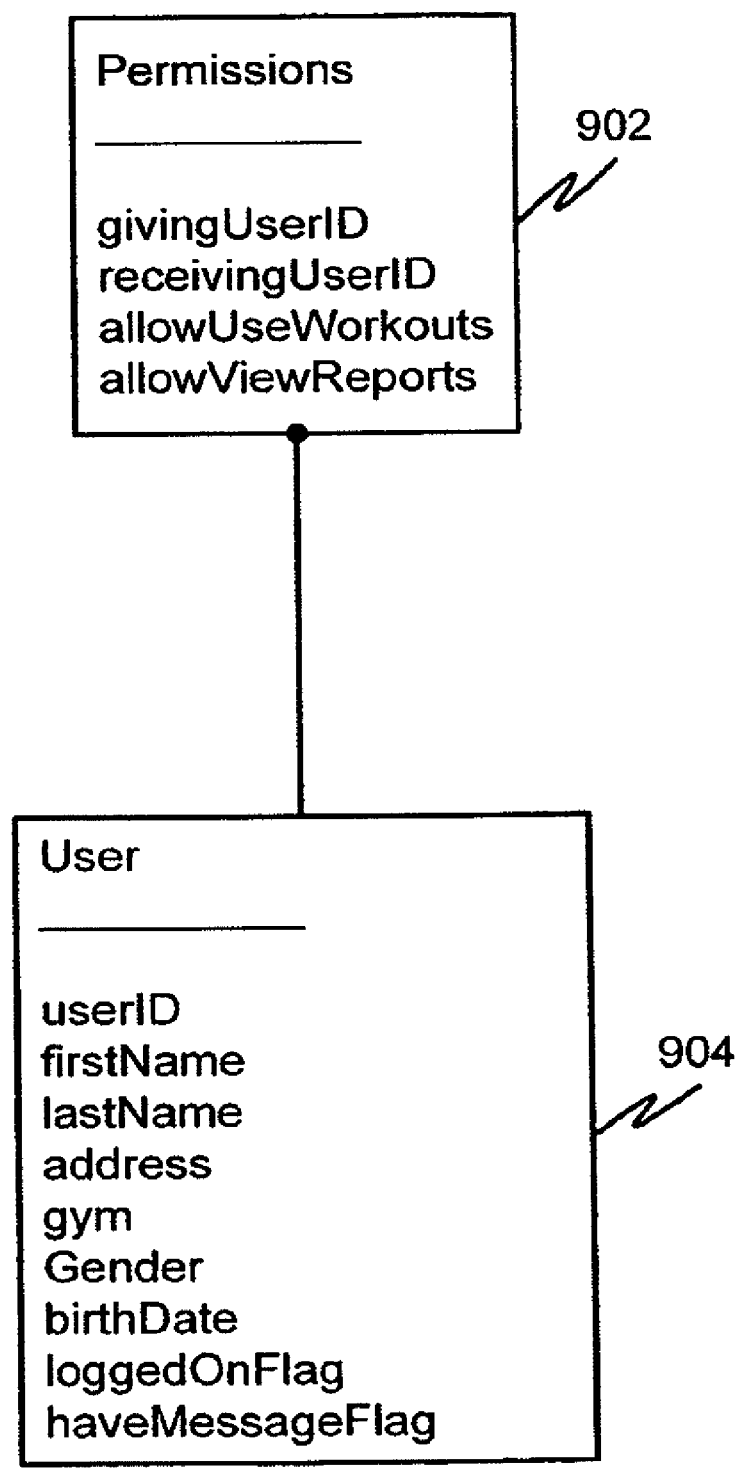
FIG. 9 is a block diagram of an exemplary relational database table to provide the capability to establish workout partners in accordance with the present invention.

FIG. 9 is a block diagram of exemplary relational database tables to provide the capability to establish workout partners in accordance with the present invention. In particular, a user table 904 has a one-to-many relationship with a permissions table 902. The user table 904 comprises fields for 1) userID, 2) firstName, 3) lastName, 4) address, 5) gym, 6) gender, 7) birthdate, 8) loggedOnFlag, and 9) haveMessageFlag. The permissions table 902 comprises four fields: 1) givingUserID, 2) receivingUserID, 3) allowUseWorkouts, and 4) allowViewReports.

The permissions table 902, through the givingUserID and receivingUserID fields, allows a user to designate one or more other users with which to share information and to partner with for working out. Flags, such as the allow use workout and allowViewReports, are used to determine the details of what information is to be shared and how information is shared between users.

Figure 10:
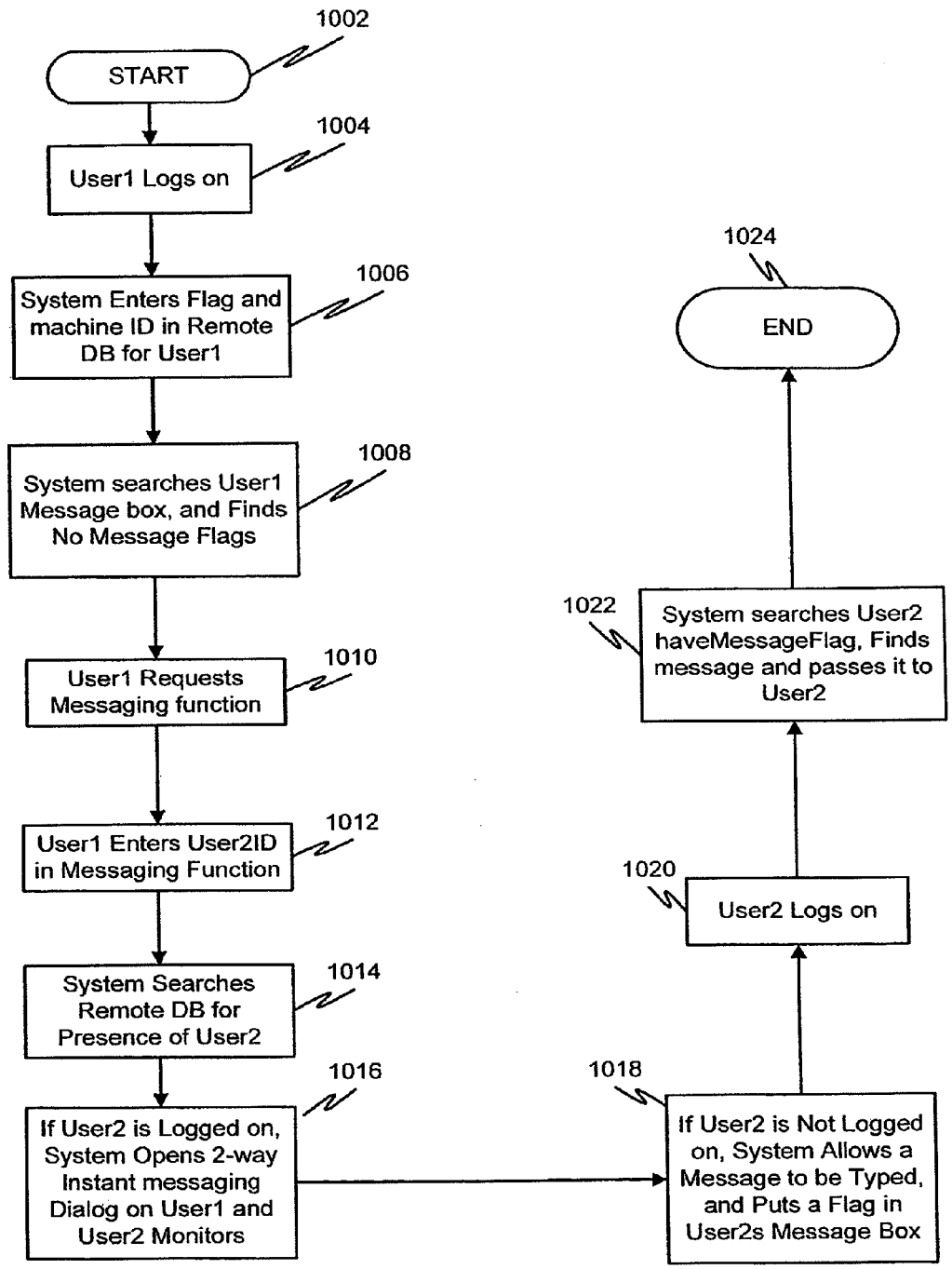
FIG. 10 is a flowchart of an exemplary method for a messaging system in the invention.

FIG. 10 is a flowchart of an exemplary method for a messaging system in the invention. In particular, the control sequence begins at step 1002 and continues to step 1004. In step 1004, a first user logs on to the graphical workout feedback system. Control then continues to step 1006.

In step 1006, the system extracts the userID and machineID from the logon transaction and stores them in a database. Control then continues to step 1008. In step 1008, the system checks the first user's message box (which may be previously established) for a flag indicating new messages. If no flag is present, control continues to step 1010.

If a new message flag were found, the first user would be alerted to the presence of a message through an on-screen visual display, an audio cue, or a combination of the above.

In step 1010, the user may request the messaging function. Control then continues to step 1012 where the first user enters a userID of a second user they want to contact. Control then continues to step 1014.

In step 1014 the system checks a user table (see for example FIG. 9, 904) for the value in the loggedOnFlag for the userID of the desired contact. If the system detects the presence of the requested contact (i.e., the second user is logged in), control then continues to step 1016 where the system opens a 2-way dialog box on the displays of both the first user and second user, and alerts the second user of the contact seeker. If the user sought does not have a "loggedOn" value in the loggedOnFlag in table 904, control passes to step 1018.

In step 1018, the system allows a message to be typed, and puts a flag in the second user's message box. When the second user logs on, control passes to step 1020. Control then passes to step 1022 where the system checks user table 904 for the haveMessageFlag for that user, finds the message and passes it to the second user. Then the control sequence ends. The control sequence may be repeated as desired or necessary to fully process messages.

Figure 11:
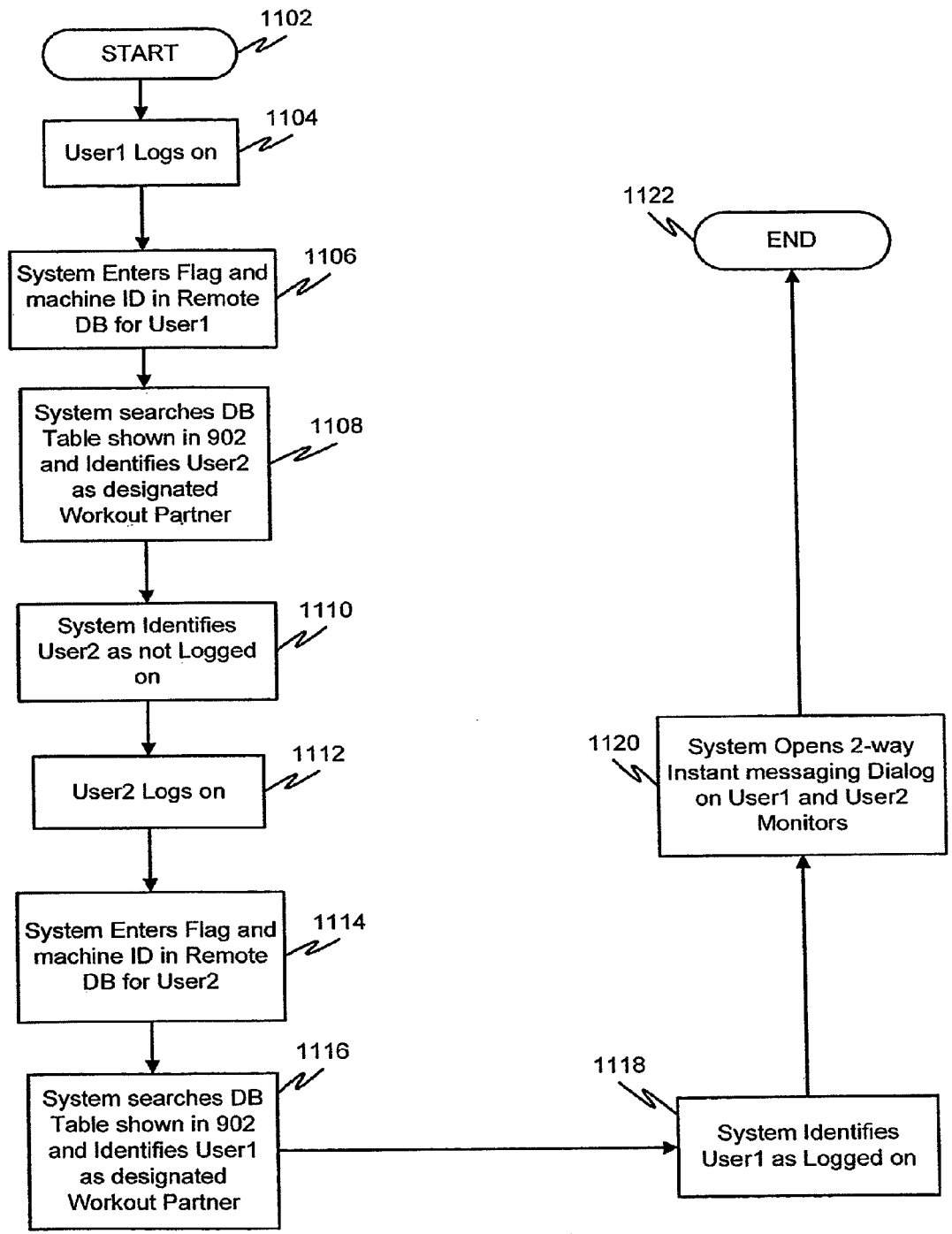
FIG. 11 is a flowchart of an exemplary method for implementing real-time communication with other users in the invention.

FIG. 11 is a flowchart of an exemplary method for the instant messaging function of the present invention. In particular, the control sequence begins at step 1102 and continues to step 1104. In step 1104, a first user (User1) logs on to the GWFS. Control then continues to step 1106. In step 1006, the system extracts the machineID from the logon transaction and stores it in a database and enters a flag indicating the first user is logged on. (For example, in the loggedOnFlag in table 904.) Control then continues to step 1108. In step 1108, the system checks for designated workout buddies of the first user, using, for example, table 902. For all designated workout buddies, the system then checks if they have a logged on indication in the loggedOnFlag in table 904. Control continues to step 1110. In step 1110, for each workout buddy the system identifies as not logged on control passes on to step 1112. In step 1112 a second user (User2) logs on who has a workout buddy who is already logged on and therefore has loggedOnFlag checked in table 904. Control then continues to step 1114.

In step 1114 the system enters a check in the loggedOnFlag in table 904 for the second user. Control then continues to step 1116.

In step 1116, the system checks the second user's designated workout buddies in table 902 and identifies the first user. Control then continues to step 1118 where the system checks the loggedOnFlag for user1 and identifies user1 as in the system. Control then passes to step 1120. In step 1120 the system opens a 2-way dialog box on each of the display systems of the first users and the second users linked by their recorded machineIDs. Then the control sequence ends, and the first and second users are able to exchange messages while working out. The control sequence may be repeated as necessary or desired to maintain communications between users of the GWFS.

Figure 12:
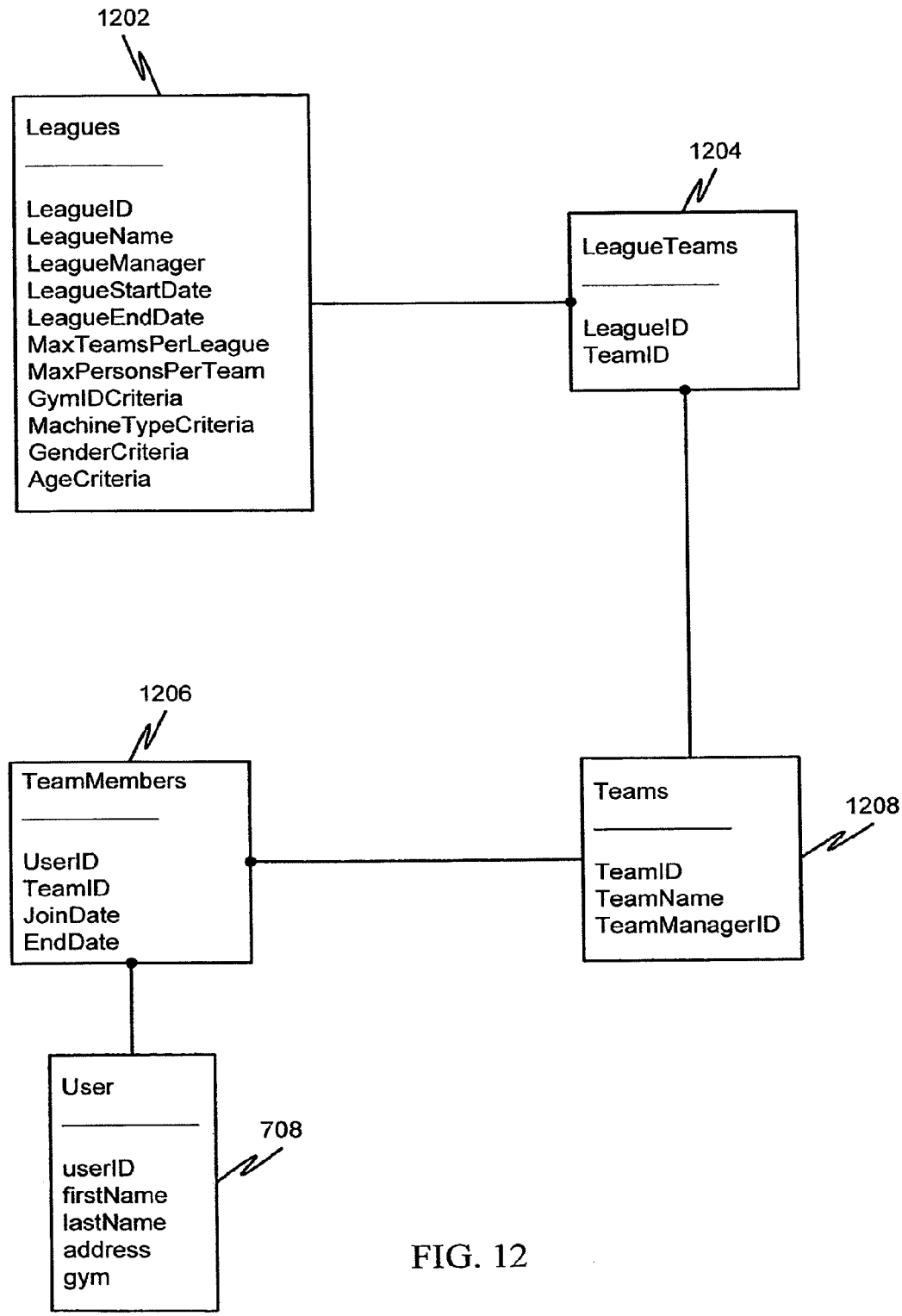
FIG. 12 is a block diagram of an exemplary relational database design for providing leagues in accordance with the present invention.

FIG. 12 is a block diagram of an exemplary relational database for providing leagues in accordance with the present invention. In particular, a leagues database 1202 is in a one-to-many relationship with a LeagueTeams database 1204. A Teams database 1208 is in a many-to-one relationship with the LeagueTeams database 1204. A TeamMembers database 1206 is in a many-to-many relationship with the Teams database 1208. And a User database 708 is in a many-to-one relationship with the Teams database 1206.

The Leagues database 1202 includes a LeagueID field for uniquely identifying the league, a LeagueName field for storing the name of the league, a LeagueManager field for storing the name of the league manager, a LeagueStartDate field, a LeagueEndDate field, a MaxTeamsPerLeague field for establishing the maximum number of teams for the league, a MaxPersonsPerTeam field for specifying the maximum number of people per team, a GymIDCriteria field used in limiting the league to one or more specific gyms, a MachineTypeCriteria for limiting the league to one or more specific machine types, a GenderCriteria for limiting the league to a particular gender, and an AgeCriteria field for limiting the league to a particular age or age range.

The LeagueTeams database 1204 includes LeagueID and TeamID fields to associate a team with a league.

The Teams database 1208 includes a TeamID field for uniquely identifying a team, a TeamName field for storing the name of the team, and a Team ManagerID field for storing the ID of the team manager.

The TeamMembers database 1206 includes UserID and TeamID fields to associate a user with a team, and JoinDate and EndDate fields to indicate when a user joined a team and left a team.

The user database is described above in relation to FIG. 7.

Figure 13:
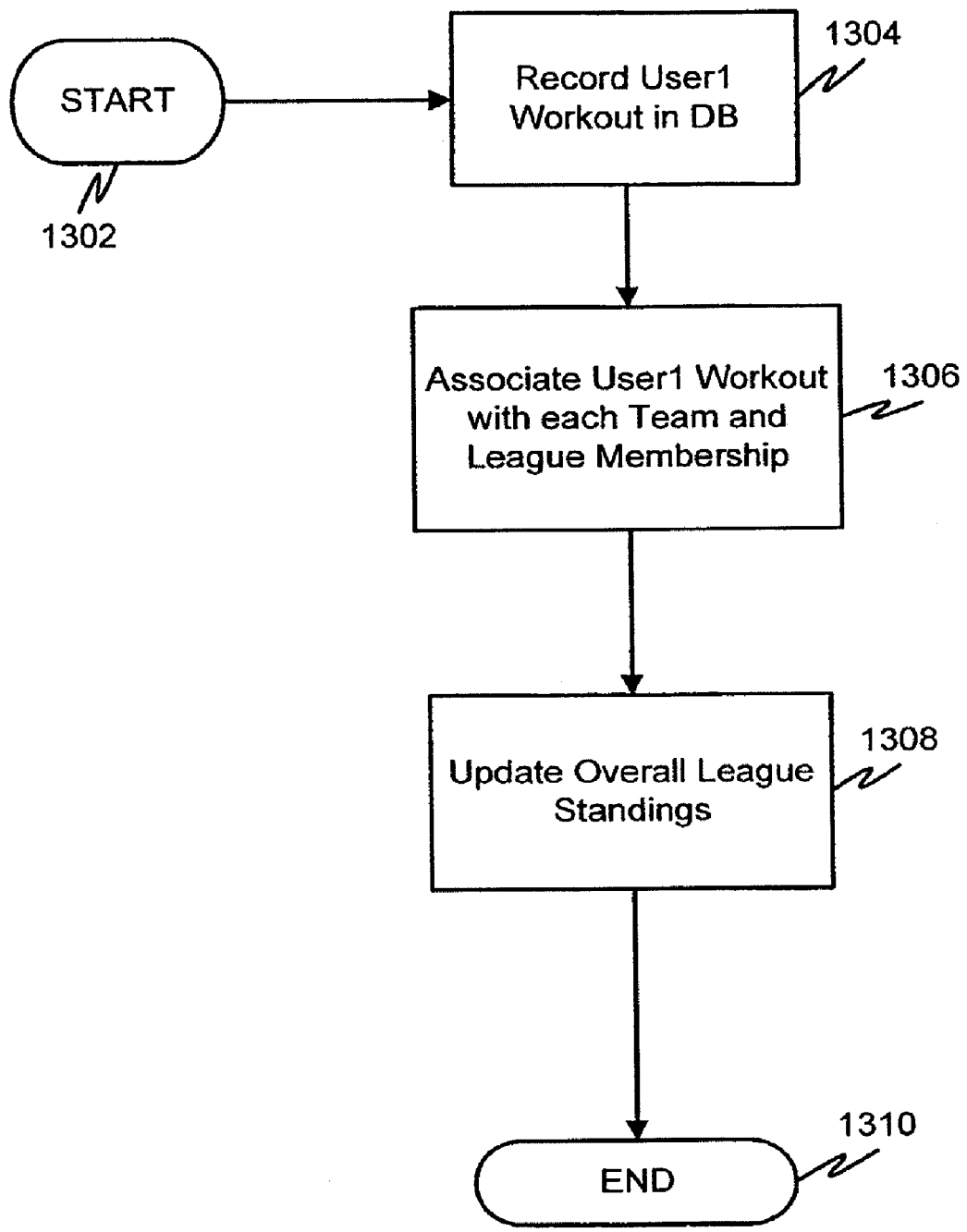
FIG. 13 is a flowchart of an exemplary method for administering leagues in accordance with the present invention.

FIG. 13 is a flowchart of an exemplary method for administering leagues in accordance with the present invention. The control sequence starts at 1302 and continues to step 1304. In step 1304, a first user (User1) is recorded in a database. Control then continues to step 1306.

In step 1306, the first user is associated with a team and league membership. Control then continues to step 1308.

In step 1308, the overall league standings are updated. Control then continues to step 1310 where the sequence ends. The control sequence of FIG. 13 may be repeated as desired or needed to update the user, team, and league data.

Figure 14:
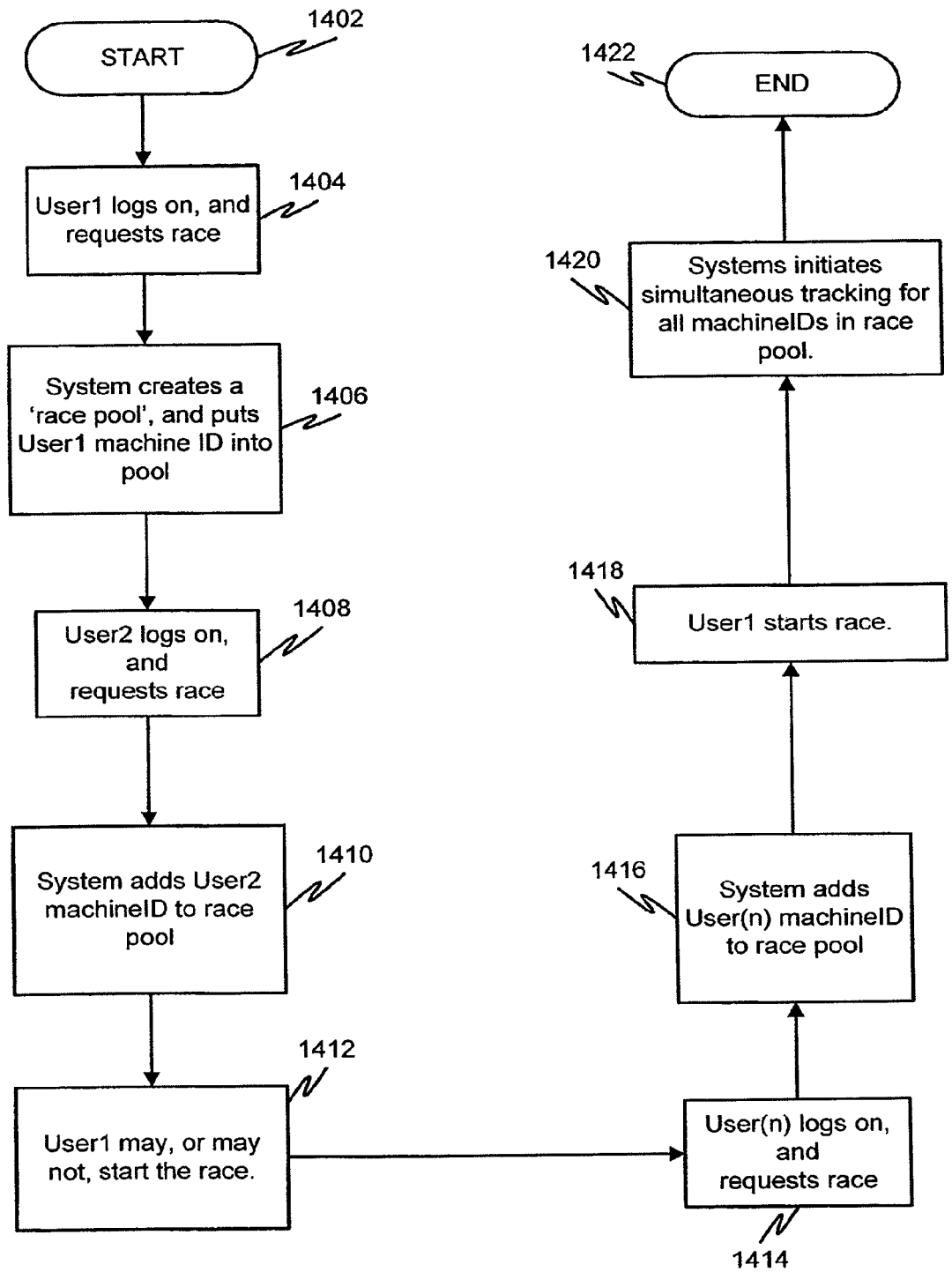
FIG. 14 is a flowchart of an exemplary method for implementing racing in accordance with the present invention.

FIG. 14 is a flowchart of an exemplary method for implementing racing in accordance with the present invention. The control sequence begins at step 1402 and continues to step 1404. In step 1404, a first user (User1) logs on and requests a race. The control sequence continues to step 1406.

In step 1406, the GWFS creates a "race pool" of competitors and puts the UserID of the first user into the race pool. The control sequence continues to step 1408.

In step 1408, a second user (User2) logs on and requests a race. The control sequence continues to step 1410.

In step 1410, the GWFS adds the second user to the race pool created in step 1406. The race pool now contains the UserIDs for the first user and the second user. Control continues to step 1412.

In step 1412, the first user may start the race, or may wish to delay starting the race to allow for other users to join. Control continues to steps 1414 and 1416. In steps 1414 and 1416, other users may log on and may be added to the race pool if they request a race. Control continues to step 1418.

In step 1418, the first user starts the race. Control continues to step 1420.

In step 1420, the GWFS initiates simultaneous tracking for all machineIDs associated with the UserIDs in the race pool. The race continues for a given time, distance, or other criteria as selected by the first user. When the race is complete results may be displayed to each user participating in the race. The control sequence continues to step 1422, when the sequence ends. The control sequence of FIG. 14 may be repeated as often as a user initiates a race request.

Figure 15:
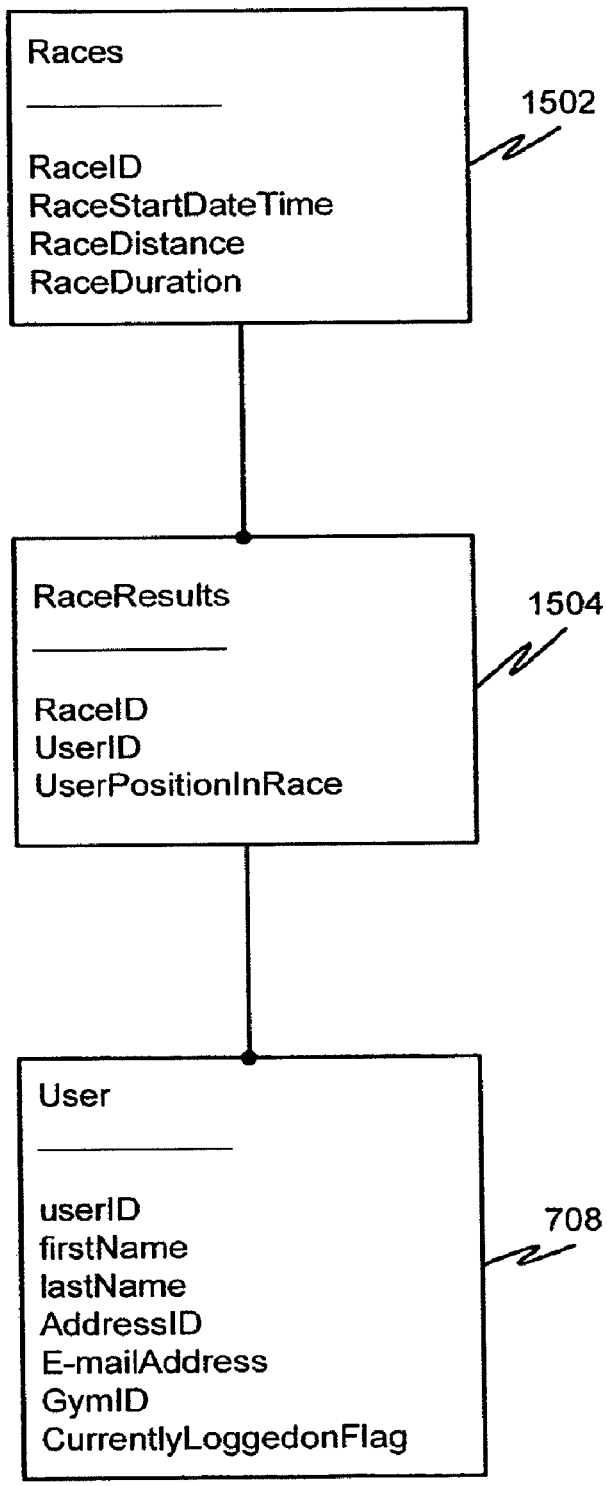
FIG. 15 is a block diagram of an exemplary relational database design for providing real-time racing in accordance with the present invention.

FIG. 15 is a block diagram of an exemplary relational database for providing real-time racing in accordance with the present invention. A Races database 1502 has a many-to-many relationship with a RaceResults database 1504. The RaceResults database 1504 has a many-to-many relationship with a User database 708.

The Races database 1502 includes a RaceID field for uniquely identifying a race, a RaceStartDateTime field for storing the start date and time of the race, a RaceDistance field for storing the distance of the race, and a Race duration field for storing the time duration of the race.

The RaceResults database 1504 includes a RaceID field for associating the results with a race in the Races database 1502, a UserID field for associating a user form the User database 708 with a race result, and a UserPositionInRace field for storing a user's finishing position in a race. The User database 708 is described above in relation to FIG. 7.

Figure 16:
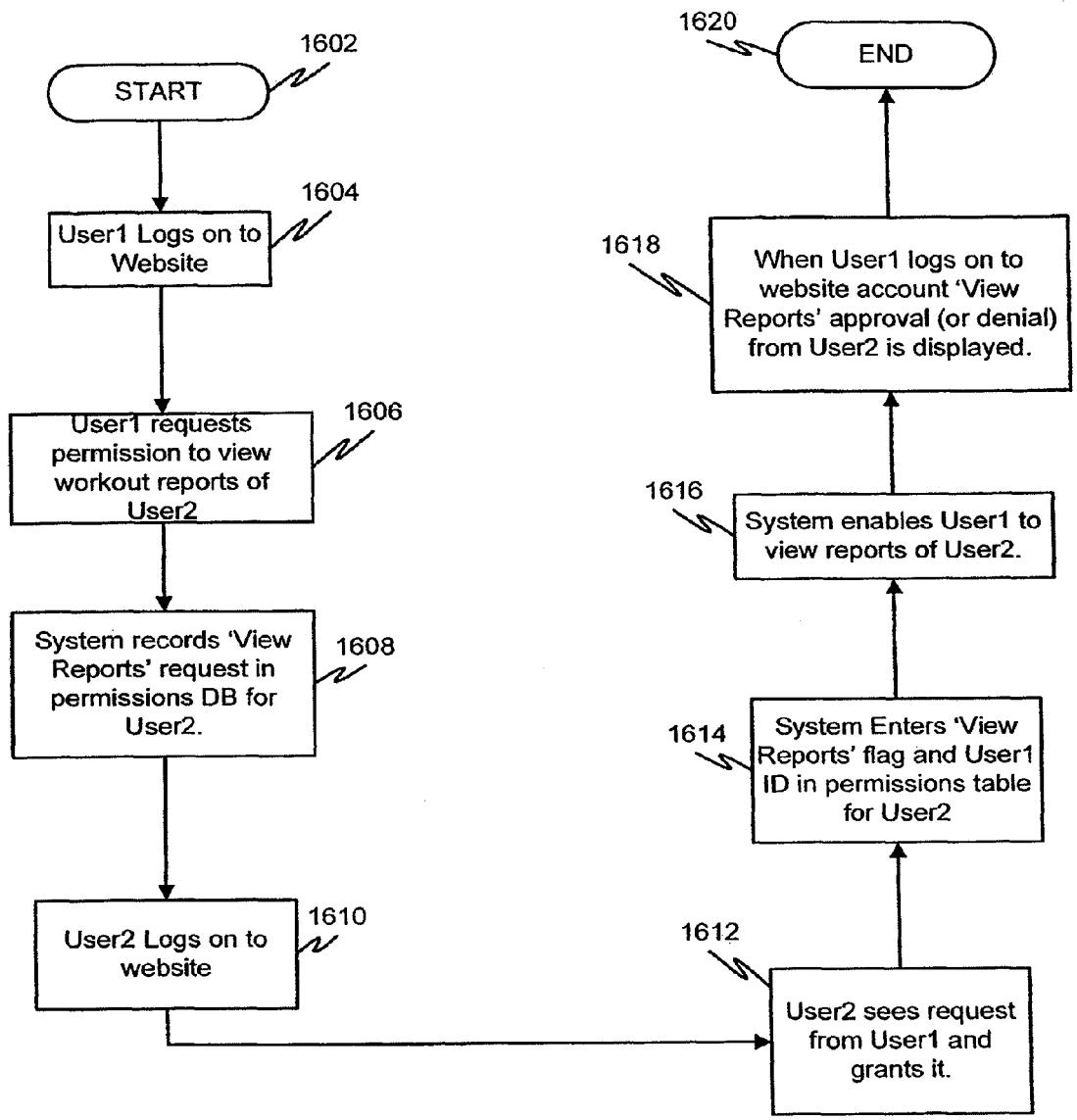
FIG. 16 is a flowchart of an exemplary method for retrieving workout reports of one user by another user.

FIG. 16 is a flowchart of an exemplary method for retrieving workout reports of one user by another user. In particular, the control sequence begins at step 1602 and continues to step 1604.

In step 1604, a first user (User1) logs onto a website coupled to the GWFS and associated databases containing workout information. Control then continues to step 1606.

In step 1606, the first user requests permission to view (or retrieve) workout reports or data of a second user (User2). Control then continues to step 1608.

In step 1608, the GWFS records the "View Reports" request in the permissions database in a field associated with the second user. Control then continues to step 1610.

In step 1610, the second user logs onto the website coupled to the GWFS and associated databases. Control then continues to step 1612.

In step 1612, the second user is presented with the request from the first user to view the workout reports of the second user. And, in this example, the second user permits the request, allowing the first user to view the workout reports of the second user. Alternatively, the second user may reject the request and the first user would not be permitted to view the workout reports of the second user. Control then continues to step 1614.

In step 1614, the GWFS sets the "View Reports" flag and the UserID of the first user in the permissions table entry for the second user. Control then continues to step 1616.

In step 1616, the GWFS enables the first user to view the workout reports of the second user. Control then continues to step 1618.

In step 1618, when the first user logs onto the website again, the acceptance of the "view Reports" request is displayed, and the first user may view or retrieve the workout reports for the second user.

The sequence shown in FIG. 16 may be used by employers, insurers, health professionals, or others, to monitor, verify, and track the workouts of selected users who have accepted the request for the viewing of their workout reports. For example, a health insurer may wish to monitor the workouts of its subscribers or customers. In another example, an employer or insurer may wish to monitor workouts to determine the usefulness and effectiveness of a fringe benefit such as a gym membership.

The graphical workout feedback method and system, as shown in the above figures, may be implemented on a general-purpose computer, a special-purpose computer, a programmed microprocessor or microcontroller and peripheral integrated circuit element, and ASIC or other integrated circuit, a digital signal processor, a hardwired electronic or logic circuit such as a discrete element circuit, a programmed logic device such as a PLD, PLA, FPGA, PAL, or the like. In general, any process capable of implementing the functions described herein can be used to implement a system for graphical workout feedback according to this invention.

Furthermore, the disclosed system may be readily implemented in software using object or object-oriented software development environments that provide portable source code that can be used on a variety of computer technologies and platforms. Alternatively, the disclosed system for providing graphical workout feedback may be implemented partially or fully in hardware using standard logic circuits or a VLSI design. Other hardware or software can be used to implement the systems in accordance with this invention depending on the speed and/or efficiency requirements of the systems, the particular function, and/or a particular software or hardware system, microprocessor, or microcomputer system being utilized. The graphical workout feedback methods and systems illustrated herein can readily be implemented in hardware and/or software using any known or later developed systems or structures, devices and/or software by those of ordinary skill in the applicable art from the functional description provided herein and with a general basic knowledge of the computer and mark-up language arts.

Moreover, the disclosed methods may be readily implemented in software executed on programmed general-purpose computer, a special purpose computer, a microprocessor, or the like. In these instances, the systems and methods of this invention can be implemented as program embedded on personal computer such as JAVA® or CGI script, as a resource residing on a server or graphics workstation, as a routine embedded in a dedicated encoding/decoding system, or the like. The system can also be implemented by physically incorporating the system and method into a software and/or hardware system, such as the hardware and software systems of an image processor.

It is, therefore, apparent that there is provided in accordance with the present invention, systems and methods for providing graphical workout feedback. While this invention has been described in conjunction with a number of embodiments, it is evident that many alternatives, modifications and variations would be or are apparent to those of ordinary skill in the applicable arts. Accordingly, applicants intend to embrace all such alternatives, modifications, equivalents and variations that are within the spirit and scope of this invention.

What is claimed is:

1. A computerized method for providing a visual gauge of fitness progress to a network of users of cardiovascular exercise machines, said method comprising:
   receiving instantaneous sensed data during a workout, the instantaneous data sensed by one or more sensors and representative of at least one workout parameter of a first user;
   storing the instantaneous sensed data as a function of time in a database having an identifier corresponding to each user;
   receiving stored historical data from one or more previous workouts, the historical data representative of the at least one workout parameter of the first user and at least one workout parameter of a second user as a function of time, said historical data retrieved with user identifiers corresponding to each of the first user and second user and being retrieved with permission of the second user;
   providing a communication link adapted for communication between the first user and the second user during the workout; and
   displaying a graphical representation of the instantaneous sensed data juxtaposed with the historical data on a display so the progress toward a desired fitness level can be gauged.

2. The method of claim 1, further comprising receiving instantaneous data from the second user concurrently with the instantaneous data of the first user when the first and second users are engaged in a virtual competition.

3. The method of claim 2, further comprising storing results of the virtual competition in the database and reporting the results to a user or an administrator of the virtual competition upon request.

4. The method of claim 3, further comprising providing a virtual competition between two or more teams of users selected from the categorized pools using instantaneous data, wherein team competition results are stored in the database and reported upon request.

5. The method of claim 4, wherein the teams of users are selected from the categorized pools using historical data of the users.

6. The method of claim 5, further comprising:
   providing the capability for individuals or teams of users to compete in leagues, wherein an interface is provided for administering the leagues, and results are stored in the database and reported upon request.

7. A nontransitory computer readable medium having stored thereon software instructions that, when executed by a processor, cause the processor to perform operations comprising:
   receiving instantaneous sensed data during a workout, the instantaneous data sensed by one or more sensors and representative of at least one workout parameter of a first user;
   storing the instantaneous sensed data as a function of time in a database having an identifier corresponding to each user;
   receiving stored historical data from one or more previous workouts, the historical data representative of the workout parameter of the first user and a second user as a function of time, said historical data retrieved with user identifiers corresponding to each of the first and second user and with permission of the second user; and
   providing a communication link for the first and second users to communicate with each other during the workout; and
   displaying a graphical representation of the instantaneous sensed data juxtaposed with the historical data on a display so that progress toward a desired fitness level can be gauged.

8. The computer readable medium of claim 7, wherein the operations further comprise:
   receiving instantaneous data from the second user concurrently with the instantaneous data of the first user when the first and second users are engaged in a virtual competition.

9. The computer readable medium of claim 7, wherein the operations further comprise:
   providing a third user with remote access to the stored historical data of the first user when the third user identifies the first user, requests to access to the historical data of the first user, and the first user grants the third user access to the historical data of the first user.

10. A system for providing an indication of fitness progress of a first user to a third party requestor, the system comprising:
    at least one sensor adapted to sense a value of at least one workout parameter during a workout of the first user and transmit the sensed value as an electronic data signal;
    a database adapted to store historical data from at least one previous workout, said historical data representative of said at least one workout parameter as a function of time;
    a processor coupled to the at least one sensor and the database, the processor being programmed to receive the sensed value and store it in the database, the stored sensed value being associated with the first user, the processor programmed to rendering a real-time graphical representation of the sensed data juxtaposed with historical data retrieved from the database;
    a display device adapted to display the rendered real-time graphical representation of the instantaneous sensed data juxtaposed with the historical data so the progress toward a desired fitness level can be gauged by the first user; and
    a server coupled to the database and adapted to provide a third-party user with remote access to the stored historical data of the first user when the third-party user identifies the first user, requests to access to the historical data of the first user, and the first user grants the request to access the historical data of the first user.

11. The system of claim 10, wherein the retrieved historical data includes historical data of the first user and historical data of a second user, different from the first user.

* * * * *